United States Patent [19] [11] 4,335,712

Trexler [45] Jun. 22, 1982

[54] ISOLATION ENCLOSURE MEMBERS

[76] Inventor: Philip C. Trexler, 2 Brook Cottage, Higgs La., Bagshot, Surrey, England

[21] Appl. No.: 130,053

[22] Filed: Mar. 13, 1980

[30] Foreign Application Priority Data

Mar. 26, 1979 [GB] United Kingdom ................ 7910495

[51] Int. Cl.³ ................ A61M 16/02

[52] U.S. Cl. ................ 128/1 R; 128/205.26; 128/1 B; 312/1

[58] Field of Search ................ 128/1 R, 1 B, 205.26; 312/1; 250/519; 252/301.1 W

[56] References Cited

U.S. PATENT DOCUMENTS

| | | | |
|---|---|---|---|
| 3,355,230 | 11/1967 | Trexler | 312/1 |
| 4,026,286 | 5/1977 | Trexler | 128/1 B |
| 4,281,691 | 8/1981 | Goutard et al. | 141/1 |

FOREIGN PATENT DOCUMENTS

| | | | |
|---|---|---|---|
| 1506930 | 11/1967 | France | 128/1 R |
| 2434464 | 3/1980 | France | 128/1 R |
| 305283 | 10/1968 | Sweden | 128/1 R |

*Primary Examiner*—Henry J. Recla

*Attorney, Agent, or Firm*—Cushman, Darby & Cushman

[57] ABSTRACT

A method of removing an article from an enclosure member providing an environment isolated from the ambient environment is particularly applicable in removing infected hospital materials from isolator enclosure members for isolating human patients with acute infectious diseases. Present methods do not satisfactorily prevent spread of infection from the removed material and maintain the integrity of the isolator. In one arrangement of the invention a disposal bag 21 sealed around a port 25 contains a closure bag 28 having a rigid hoop 30 across the disposal bag 21. Heat sealer 33 cuts and seals around the hoop leaving part of closure bag 28 closing the disposal bag 21 and part of bag 28 closing transfer port 25. In another arrangement closure bag 28 slides over a rigid former 34 extending outwardly from the transfer port and cutter sealer 33' cuts and seals portions of the closure bag across the disposal bag by cooperating with a backing member 29' in the closure bag 28. In both arrangements the interior surface of the closure bag 28 is medically clean and after cutting and sealing the surface forms outer surfaces of the disposal bag 21 and transfer port 25.

17 Claims, 14 Drawing Figures

Figure 3C:
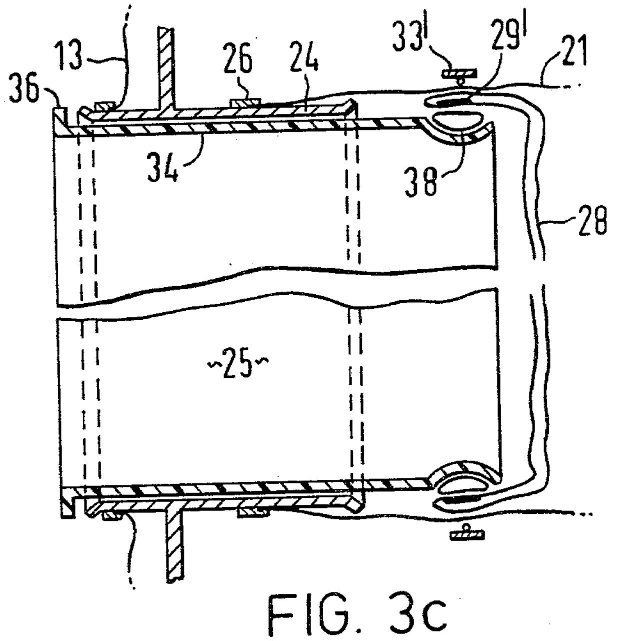

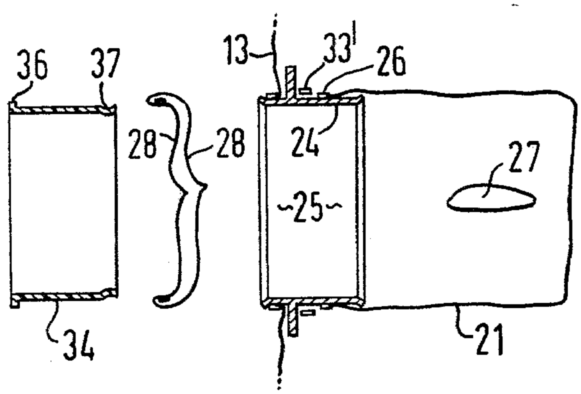
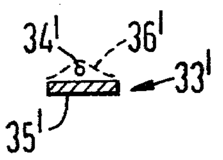
FIG. 3e
FIG. 3a
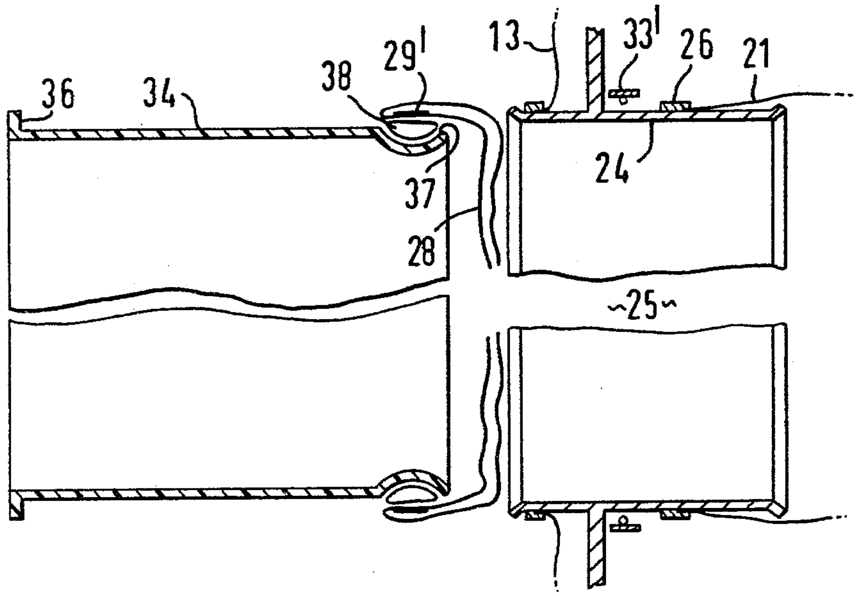
FIG. 3b

ISOLATION ENCLOSURE MEMBERS

The present invention relates to enclosure members for providing an environment isolated from the ambient environment, and is concerned in particular but not exclusively with such enclosure members for isolating human patients with acute infectious diseases such as acute viral haemorrhagic fevers, for example Lassa fever.

It is known to use enclosure members for the handling of laboratory animals and human patients under controlled microbiological conditions and such enclosure members have become known as "isolators." An isolator commonly consists essentially of a flexible transparent bag of synthetic plastics material forming an anclosure which is vented with germ-free air. Often the enclosure member is of disposable form, being provided presterilised for use on one occasion only.

Isolators are of two main kinds, namely so called "exclusion isolators" and so called "containment isolators." In exclusion isolators, the germ-free air in the enclosure of the isolator is normally maintained at a higher pressure than the ambient atmospheric pressure by continuously supplying filtered air to the enclosure and allowing air to escape from the enclosure from a pressure valve or otherwise. The pressurised air flow serves to exclude microbes in the ambient surroundings from the enclosure of the isolator if the isolating barrier is accidentally ruptured or when sterile materials are introduced through an emerging air stream at a transfer port. In containment isolators the air is normally maintained at a lower pressure than ambient atmospheric pressure by withdrawing air from the enclosure via a filter. Usually air is continuously supplied to and withdrawn from the container, requiring filters on both the air inlet and air outlet. The lower pressure of air within the enclosure member serves to contain microbes within the enclosure member if the isolating barrier is accidentally punctured thus preventing for example, spread of infection from a patient within the containment isolator to the ambient surroundings of the enclosure member. The pressure differential between enclosure of the isolator and the ambient atmosphere exerts a force upon the isolator walls tending to collapse the isolator, so that a rigid frame is generally necessary to maintain the isolator in its erected condition. The present invention is concerned with isolators when used in the containment mode.

In all isolators, the main weakness in the isolation of the system lies in the arrangements for introducing and removing material and instruments into and out from the enclosure member, as these arrangements usually involve the need to break the boundary of the environment. A particular problem occurs when removing contaminated articles from a containment isolator, in that it is not only necessary to maintain the integrity of the isolation enclosure member during the removal of the article, but it is also necessary to maintain the contaminated article in a sealed condition after leaving the enclosure member, so as to prevent spread of infection to the ambient surrounds from the contaminated article which has been removed. A difficult situation in which this problem occurs is in a hospital where the contaminated article comprises materials such as used bandages, soiled linen and bed pans which need to be removed from a containment isolator housing a patient having an infectious disease.

The present practice is to put the contaminated material into the end of a wide replaceable disposal bag extending from the containment isolator, to bunch the bag together between the contaminated material and the main body of the isolator and to tie as tightly as possible the bunched bag with two plastic straps spaced a short distance apart. The bunched and bound bag is then cut by an awkward and laborious process involving a soldering gun, and the contaminated material in the bag is then placed in a further bag which is heat sealed using a commercial bag sealer and then disposed of, for example, by burning. The seal left on the bag of contaminated material is known not to be entirely secure but the alternative method (used sometimes in the laboratory), of stretching the sleeve out flat and closing it off with a heat seal, is inapplicable in hospital conditions because of the difficulty of obtaining a secure heat seal across a long area of a stretched heavily loaded bag.

It is an object of the present invention to provide improved arrangements for removing contaminated articles from an isolation enclosure member used in the containment mode.

According to the present invention there is provided a method of removing an article from an enclosure member providing an environment isolated from the ambient environment comprising the steps of passing the article through a port in the enclosure member into a disposal bag communicating with the port, positioning within the disposal bag a closure member comprising a closed bag having a clean inner surface, arranging the closure bag across the disposal bag to form a double-walled barrier between the port of the enclosure member and the article in the disposal bag, and effecting a sealing and cutting operation around the disposal bag in the region of the closure bag to cut through the disposal bag and the closure bag and to leave a portion of the closure bag sealed across the disposal bag on each side of the cut with the said clean surface of the closure bag exposed to the ambient environment, the article being sealed in the severed part of the disposal bag by one portion of the closure bag and the remainder of the disposal bag being closed by the other portion of the closure bag.

Conveniently there may be provided within the closure bag a backing member for cooperation with a sealing and cutting device for effecting the sealing and cutting step, the method including the step of arranging part of the closure bag and part of the disposal bag in a sandwich between the backing member and the sealing and cutting device during the sealing and cutting operation.

Conveniently the backing member may comprise a hoop member and the method may include the steps of arranging the hoop member generally transverse to the disposal bag in a position such that the closure bag spans the hoop member and part of the closure bag is sandwiched between the hoop member and the disposal bag.

In accordance with one aspect of the invention, the hoop member may be a substantially rigid member, and the method includes the step of applying inward pressure against the sandwiched portions of the closure bag and the disposal bag against the rigid hoop member during the sealing and cutting operation. Preferably the sealing and cutting operation is effected by a heated cutting element applied to the outer surface of the disposal bag around the hoop member, so that there is provided a sandwich of elements comprising, in the order given, the heating element, a part of the disposal bag, a part of the closure bag, and the hoop member.

In this aspect of the invention, preferably the hoop member comprises an inner, relatively stiff support portion, and an outer, relatively soft resilient layer allowing a good seal to be obtained by inward pressure of the heating element against the hoop member.

Preferably the hoop member is of circular shape, as is the said port in the enclosure member, but it is to be appreciated that the hoop member may be of shape of other than circular, for example oval, especially where the port is of shape other than circular. In some arrangements the hoop member need not be a continuous member but may for example be a spiral or helix member, or may be a generally circular member having a small portion of overlap with one end of the member passing over the overlapping other end of the member.

In accordance with another aspect of the invention, the backing member may comprise a flexible member, and the method may include the steps of sliding the backing member onto one end of a hollow former of approximately the same cross-section as the disposal bag so that an adjacent pair of walls of the closure bag span one end of the former, advancing the former from the enclosure member through the port into the disposal bag so that the closure bag forms a barrier across the disposal bag with a portion of the closure bag sandwiched between the backing member and the inner surface of the disposal bag, applying around the disposal bag in the region of the backing member a cutting and sealing device, activating a pressure member positioned between the former and the closure bag so as to exert an outward pressure on the backing member to bring the adjacent layers of the closure bag and the disposal bag into operative contact with the cutting and sealing device, and effecting the said sealing and cutting operation.

Preferably the step of activating the pressure member comprises inflating an expandable pressure member which is arranged around the former. Conveniently the inflatable pressure member consists of a rubber annular tube such as an inner tube of a bicycle.

In both aspects of the invention, the said sealing and cutting step may be effected by a heating element known in itself and referred to as an impulse sealer. Such elements are well-known for effecting a simultaneous cutting and sealing operation on two or more sheets of flexible synthetic plastics material so as to leave the sheets sealed to each other on either side of the cut.

Preferably the enclosure member is a flexible walled enclosure member formed of flexible synthetic plastics material, and preferably the disposal bag and the closure bag are also made of flexible synthetic plastics material.

In accordance with the first aspect of the method of the invention as set out above, it is preferred that the hoop member comprises a short cylindrical member having for example a depth along its axis in the range 0.1 to 0.02 times its diameter across a circular cross-section of the hoop member. Where the hoop member is rigid, the hoop member may be for example of rigid polyvinyl chloride. In the second aspect of the invention where the member is a flexible member, this may conveniently be made of for example relatively thick PVC or rubber, or conveniently the flexible backing member may comprise adhesive neoprene or polyurethane foam tape stuck to one inner surface of the closure bag. In preferred arrangements of the invention, it is an important requirement that the backing member shall be capable of withstanding high temperatures produced by a heated element sealing and cutting device, and also that the backing member is of material such that the sheets of synthetic plastics material forming the two bags do not stick to the backing member after the cutting and sealing operation.

The terms "rigid," "stiff," and "flexible" are intended to be relative terms and to indicate a degree of stiffness or rigidity relative to the function of the element. Thus where the backing member is a rigid member, it should be sufficiently rigid to allow the cutting and sealing step to be carried out by inward pressure against the backing member. Where the backing member is a flexible member it should conveniently be sufficiently stiff to be easily manoeuvred in or with the bag, and yet sufficiently flexible to enable it to slide over the said former. The former should conveniently be sufficiently rigid to allow the activation of the pressure member to produce the required outward pressure in cooperation with the cutting and sealing device. The closure bag, disposal bag and other parts of the enclosure member are preferably of flexible synthetic plastics material of the kind known to be used in isolators.

There is also provided in accordance with the present invention in the said first aspect an enclosure member for providing an environment isolated from the ambient environment, the enclosure member having a flexible disposal bag having one end coupled to the enclosure member around a transfer port for passage of objects out of the enclosure member, a closure bag comprising a closed bag having a clean inner surface and containing a backing member in the form of a hoop adapted to be positioned within the disposal bag and to be arranged generally transverse to the disposal bag in a position such that the closure bag spans the hoop member to form a double walled barrier across the disposal bag and that part of the closure bag is sandwiched between the hoop member and the disposal bag, and means for effecting a sealing and cutting operation around the hoop member to cut through the disposal bag and the closure bag and to leave a portion of the closure bag sealed to the disposal bag on each side of the cut with the said clean surface of the closure bag exposed to the ambient environment, the article being sealed in the severed part of the disposal bag by one portion of the closure bag and the remainder of the disposal bag being closed by the other portion of the closure bag after the sealing and cutting operation.

There is further provided in accordance with the said second aspect of the present invention an enclosure member for providing an environment isolated from the ambient environment, the enclosure member having a flexible disposal bag having one end coupled to the enclosure member around a transfer port for passage of articles out of the enclosure member, a hollow former of approximately the same cross-section as the disposal bag, a closure bag comprising a closed bag having a clean inner surface, the closure bag being adapted to slide onto one end of the hollow former so that an adjacent pair of walls of the closure bag span one end of the former, the former being of a size such as to allow advance of the former from the enclosure member through the port into the disposal bag so that the closure bag forms a barrier across the disposal bag with a portion of the closure bag sandwiched between the former and the inner surface of the disposal bag, a pressure member positioned between the former and and closure bag for exerting, when activated, an outward pressure on the closure bag, and means for effecting a sealing and cutting operation around the disposal bag in the region of the closure bag by cooperation between the sealing and cutting means and the pressure member to cut through the disposal bag and the closure bag and to leave a portion of the closure bag sealed across the disposal bag on each side of the cut with the said clean surface of the closure bag exposed to the ambient environment.

Where, in accordance with both the method and apparatus of the invention, reference is made to the closure bag having a clean inner surface, the term clean means at least clean to the extent of being uncontaminated by the environment within the enclosure member. Conveniently the inner surface is clean to the same standard as the ambient environment.

The various preferred features of the invention which have been set out in accordance with the methods of the invention are also provided in accordance with the apparatus of the invention. In particular, there may be provided in accordance with both aspects of the apparatus of the invention a backing member for cooperation with the heating and sealing means. In accordance with the first aspect of the invention, the backing member may comprise a hoop member which is a substantially rigid member adapted to be arranged with the said part of the closure bag sandwiched between the outside of the hoop member and the inside of the disposal bag, and adapted to allow the sealing and cutting step to be effected by application of a heating element around the hoop member with inward pressure onto the hoop member. In accordance with the second aspect of the apparatus of the invention, the closure bag may contain a flexible backing member adapted to slide over the said former to position the closure bag to form the said barrier, and to cooperate with the cutting and sealing means. In such an arrangement the pressure member is arranged to exert outward pressure on the backing member to carry the appropriate portions of the two bags into operating relationship with the cutting and sealing means.

There is also provided in accordance with the present invention an isolator component suitable for use in accordance with the method of the invention as set out hereinbefore, the component consisting of a closure bag comprising a flexible closed bag containing a backing member, the bag being adapted for a sealing and cutting operation around the backing member within a flexible disposal bag extending from a port in an enclosure member, as set out hereinbefore.

Figure 1:
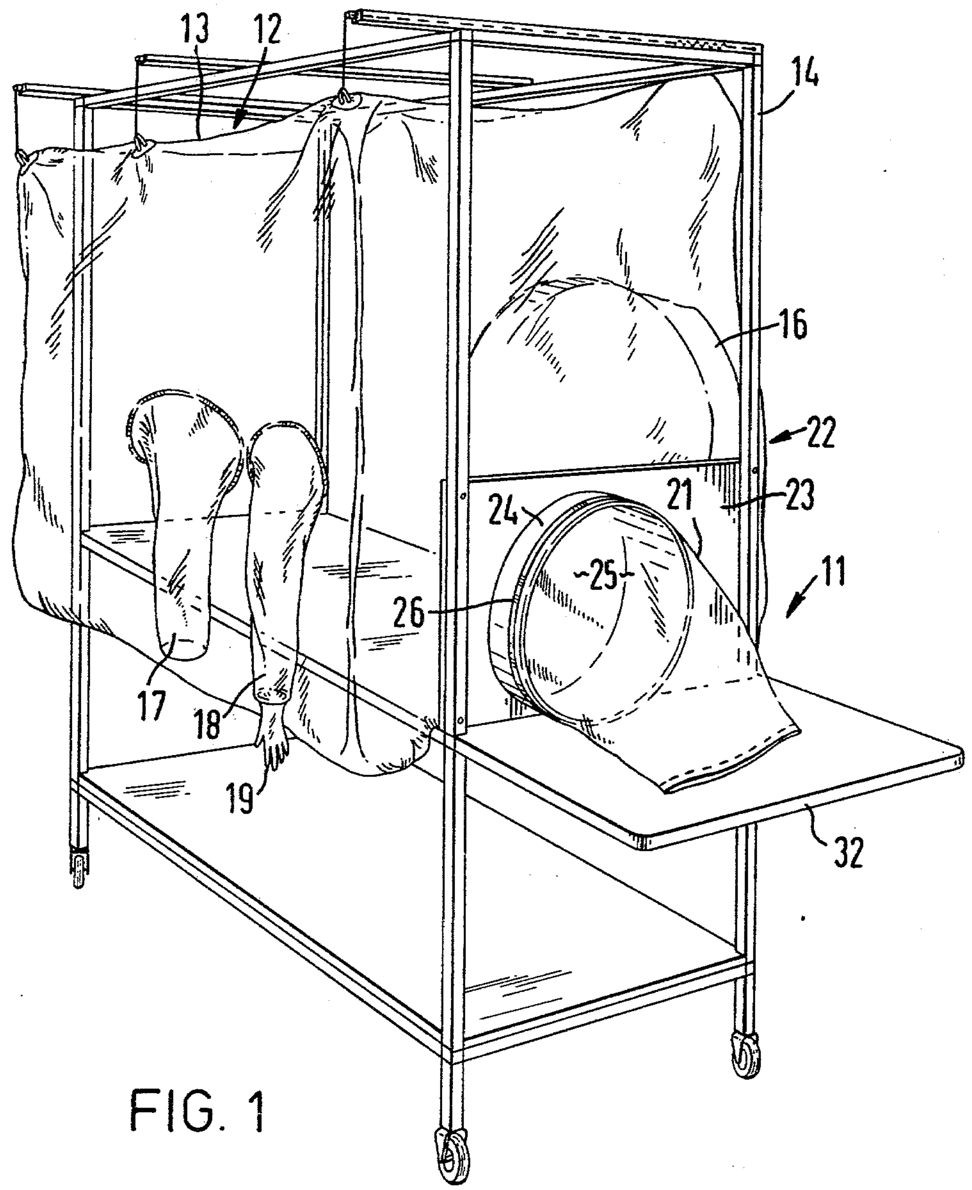
Figure 2A:
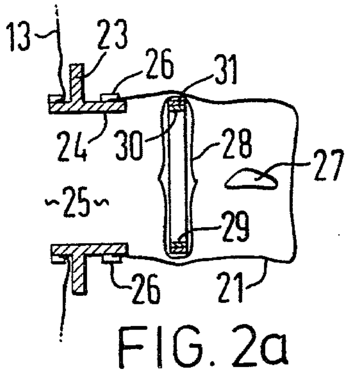
Figure 2D:
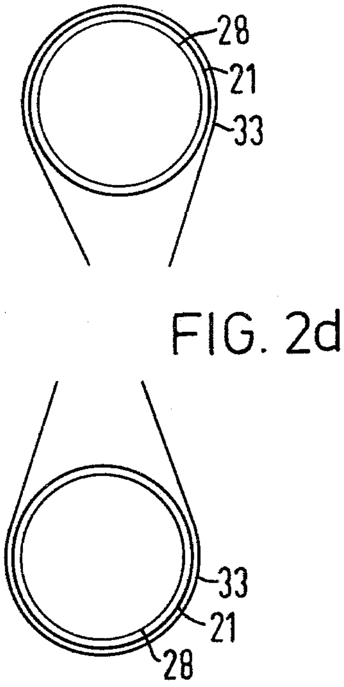
Figure 2B:
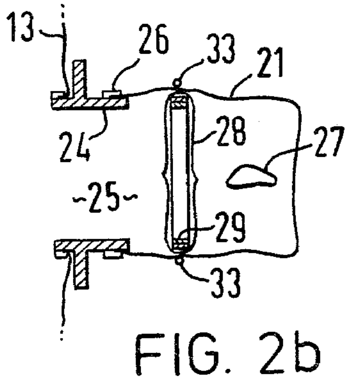
Figure 2E:
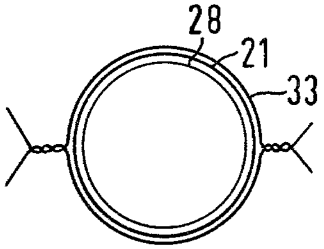
Figure 2C:
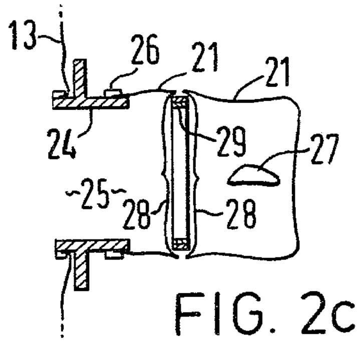
Figure 3D:
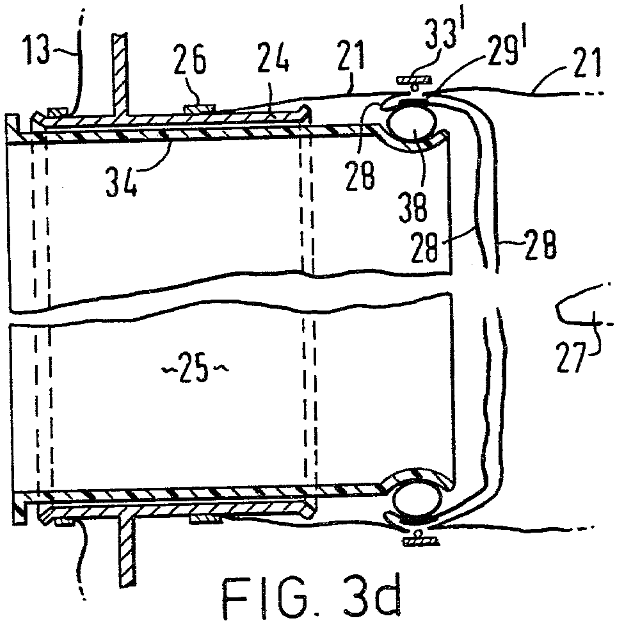

Embodiments of the invention will now be described with reference to the accompanying drawings in which:

FIG. 1 shows an isolation enclosure member having an outlet port adapted for use in accordance with the method and apparatus of the present invention for removing contaminated articles from the enclosure member;

FIGS. 2(*a*) to 2(*e*) are diagrammatic representations in cross-section showing a series of steps in accordance with the method of the present invention in a first aspect for removal of a contaminated article from the enclosure member;

FIGS. 3(*a*) to 3(*e*) are diagrammatic representations showing in cross-section a series of steps in the method according to the invention in a second aspect for removing a contaminated article from an enclosure member; and FIGS. 4(*a*) to 4(*c*) are diagrammatic representations showing in cross-section a series of steps in a convenient method of manufacturing a closure bag suitable for use in the method described with reference to FIGS. 3(*a*) to 3(*e*).

Referring firstly to FIG. 1 there will be described an enclosure member 12 adapted for use as a supply isolator in the containment mode and having a transfer port assembly indicated generally at 11. The enclosure member 12 is generally arranged as a supply isolator of conventional design, and will be referred to hereinafter as the supply isolator 12. The main envelope 13 of the supply isolator 12 is suspended from a metal frame 14 and coupled via a relatively large opening 16 to a bed isolator which is not shown. The supply isolator 12 has two flexible sleeves 17 and 18 which are either supplied with or adapted to cooperate with gloves 19 to allow manipulation in known manner of objects within the supply isolator 12.

The purpose of a supply isolator is to provide a transfer area in which objects needed in a bed isolator can be assembled and can be passed into and out of the main bed isolator. The supply isolator will normally also receive any required articles into the supply isolator through the transfer port 11, which is also used for passage of contaminated goods out of the supply isolator 12. The contained microbiological environment consists of the whole of the interior of the supply isolator and the whole of the interior of the bed isolator which communicates with the supply isolator. The pressure within the supply isolator is maintained below atmospheric pressure by a pump and air enters the isolator through a filter port (not shown).

The transfer port assembly 11 shown in FIG. 1 is suitable for use in combination with other elements to be described hereinafter for passage of contaminated material out through the port assembly 11 in either of two aspects of the invention, which are described respectively with reference to FIGS. 2(*a*) to 2(*e*) and FIGS. 3(*a*) to 3(*e*).

Referring again to FIG. 1, the transfer port assembly 11 includes a flexible disposal bag 21 coupled to the supply isolator 12 by means of a frame 22. The frame 22 comprises a flat plate 23 fastened to the metal frame 14, and a short rigid cylinder 24 projecting outwardly from the plate 23 and inwardly towards the interior of the isolator 12. The rigid cylinder 24 defines an opening or port 25 communicating with the interior of the supply isolator 12. In a simple arrangement, the walling of the isolator 12 may be secured for example by welding or taping to the rear of the plate 23 so that the opening 25 in the plate 23 provides direct access to the interior of the supply isolator 12. Also in such a simple arrangement, the flexible bag 21 can be secured by a rubber band, or otherwise, at 26, around the outside of the cylinder 24 at its outer end. (In other arrangements, the main wall of the isolator 12 may include a sleeve which protrudes through the cylinder 24 and provides a liner for the cylinder. However such an arrangement is not relevant to the present invention, and is omitted for the sake of simplicity).

Conveniently there may be provided a projecting shelf 32 secured to the main framework 14 for supporting the disposal bag 21 and objects placed therein during operation of the transfer port assembly.

Referring now to FIGS. 2(*a*), (*b*) and (*c*) there will be described the steps in the method of the invention in a first aspect. The initial step, before the stage shown in FIG. 2(*a*), is to pass through the opening 25 the contaminated article 27 into the disposal bag 21. The next stage, shown in FIG. 2(*a*), is to position within the disposal bag 21 a closure bag 28 comprising a closed bag of flexible synthetic plastics material containing a rigid hoop member 29. At least the inner surfaces of the closure bag 28 (and the surface of the hoop member 29) are clean relative to the interior of the isolator 12. Preferably the closure bag 28 is made of the same material as the bag 21. The hoop member is arranged generally transverse to the length of the disposal bag 21 in a position such that the closure bag 28 spans the hoop member 29 to form a barrier across the disposal bag 21. The position is also such that part of the closure bag 28 around the outer perimeter of the hoop member 29 is sandwiched between the outer surface of the hoop member 29 and the inner surface of the disposal bag 21.

Conveniently the hoop member consists of a short cylinder of rigid polyvinyl chloride cut from a pipe. Conveniently the internal diameter may be 44 cms., the thickness of the piping 4 mm., and the depth of the short cylinder along its axis 3.5 cms. This rigid piping forms an inner component 30 of the hoop member 29, which also includes an outer component 31 consisting of adhesive backed silicone foam, for example 4 mm. deep, which is stuck to the outer surface of the piping 30 before insertion into the closure bag 28.

The next stage in the method is shown in FIG. 2(*b*) and consists of positioning around the outside of the hoop member 29 a heating element 33 which may either comprise a complete circle around the member 29, or may comprise two lengths of heating element each of which encircles slightly greater than a semicircle of the hoop member 29 so as to leave a small area of overlap and to provide a complete encirclement of the hoop member 29. Such a method of heating and sealing is shown diagrammatically in FIG. 2(*d*). An alternative method is shown in FIG. 2(*e*) in which two lengths of hot wire sealing element are wound around respective halves of the material to be sealed and are then twisted around each other and brazed to form a permanent sealer. Conveniently the heating element 33 comprises a hot wire sealer of known design.

The heating element 33 is applied in such a manner that there is sandwiched between the hoop member 29 and the heating element 33 part of the closure bag 28 and part of the disposal bag 21. There is next passed through the heating element 33 a current sufficient to effect between the sandwiched portions of the closure bag 28 and disposal bag 21 a sealing and cutting operation around the hoop member to cut through the two bags and to leave a portion of the closure bag 28 sealed to the disposal bag 21 on each side of the cut. The effect of this is shown in the final stage of the method illustrated in FIG. 2(*c*). At this stage the article 27 is sealed in the severed part of the disposal bag 21 by one portion of the closure bag 28, and the remainder of the disposal bag 21 is closed by the other portion of the closure bag 28. The hoop member 29 then becomes free to be removed, and can be reused in a further closed bag for removing further material from the isolator. It is to be appreciated that the FIGS. 2(*a*) to 2(*c*) show the method only in a diagrammatic form.

It is to be appreciated that the foam backing 31 on the hoop member 29 allows the heating element 33 to be tightened around the hoop member 29 to effect a good seal during the cutting and sealing operation.

Referring now to FIGS. 3(*a*) to 3(*e*), the method of the invention will now be described in a further embodiment, illustrating a second aspect of the invention. Elements common to the elements shown in FIG. 1 and FIGS. 2(*a*), (*b*) and (*c*) will be referred to my like reference numerals. Referring to FIG. 3(*a*), the first stage of the method is similar to that shown in FIG. 2(*a*), in that the article 27 to be removed from the enclosure member 12 is again passed through the opening 25 into the disposal bag 21. FIG. 3(*a*) shows the main components of the apparatus at the initial stage, and there is provided within the enclosure member 13 a former 34 and a closure bag 28. The former 34 comprises a short cylindrical member formed of rigid PVC and having an outer diameter slightly less than the inner diameter of the cylinder 24 so as to allow the former 34 to pass as a loose sliding fit through the cylinder 24. The former 34 is longer than the cylinder 24 so as to allow the right hand end of the former 34 in FIG. 3(*a*) to protrude through the cylinder 24 into the disposal bag 21 when pushed into position as will be described hereinafter with reference to FIG. 3(*c*). The former 34 carries at its left hand end (in FIG. 3(*a*)) a flange 36 which provides a stop for the former 34 when inserted into the cylinder 24. At its right hand end the former 34 has an annular groove 37 around its outer surface, sufficient to accept an inflatable pressure member which, conveniently may comprise a bicycle inner tube (shown in FIGS. 3(*b*) to 3(*d*)).

Referring now to FIG. 3(*b*), the closure bag 28 contains a backing member 29′ of flexible material which, as will be described hereinafter, is stuck to one inner surface of the closure bag 28. The backing member 29′ may conveniently be formed of adhesive neoprene or polyurethane foam tape. The first step of the method, after the article 27 has been passed into the disposal bag 21, is that the backing member 29′ is positioned by sliding over the inflatable pressure member 38 in the groove 37 in the end of the former 34. The bag 28 is held in place over the member 38 by adhesive tape with closure bag 28 forming a double walled barrier across the end of the former 34. At this stage there is arranged around the cylinder 24 a heating element 33′ which is shown in detailed cross-section in FIG. 3(*e*). Conveniently the heating element 33′ comprises a heating wire 34′, for example a conducting wire, backed by a high temperature resistant rigid strip 35′ and covered by a strip of glass cloth 36′. The glass cloth 36′ is conveniently coated with Teflon which allows heat to penetrate the plastics material to be sealed without the plastics sticking to the element 34′. The strip 35′ serves to hold the edges of the plastics materials to be cut and sealed (to prevent tearing) by serving as a clamp against the member 38 when inflated. The heating device 33′ conveniently operates on low voltage alternating current of a value depending on the length and gauge of the wire, but sufficient to bring the wire to the required heat. Such heaters are well-known in the art for melting and sealing, for example polythene at 110° C., and will not be described in detail in this specification.

The next step after the closure bag 28 has been arranged with the backing member 29′ over the inflatable pressure member 38, is that the former 34 is advanced into and through the cylinder 25 as shown in FIG. 3(*c*) until the stop 36 reaches the inner end of the cylinder 24. In this position the closure bag 28 forms a double walled barrier across the disposal bag 21 and part of the closure bag 28 is sandwiched between the backing member 29′ and the inner surface of the disposal bag 21.

Also at the stage shown in FIG. 3(*c*), the heating element 33' has been positioned over the backing member 29' by sliding the heating element 33' along the outside of the disposal bag 21.

The next stage, as shown in FIG. 3(*d*) is that the inflatable pressure member 38 is inflated by an air line passing from the pressure member 38 back through the opening 25 into the interior of the enclosure member 13 (the air line not being shown in the Figures). This inflation produces an outward pressure on the backing member 29' which brings the appropriate sandwiched portions of the closure bag 28 and disposal bag 21 into close operating contact with the heating element 33'. The next step is that the heating element 33' is activated to effect the required cutting and sealing operation, which as shown in FIG. 3(*d*) effects a cut through the disposal bag 21 and the closure bag 28 to leave a portion of the closure bag 28 sealed across the disposal bag 21 on each side of the cut with the clean inner surface of the closure bag exposed to the ambient environment. As shown in FIG. 3(*d*) the article 27 is sealed in the severed part of the disposal bag 21 by one portion of the closure bag 28, and the remainder of the disposal bag 21 is closed by the other portion of the closure bag 28.

It is an advantage of the method which has been described with reference to FIG. 3(*a*) to 3(*e*) that the closure bag 28 with its backing member 29' can be folded flat to form a package easily stored and easily kept in the enclosure member before use. The former 34 which has been used for removing the article 27 can afterwards be withdrawn back into the interior of the enclosure member 13 for use again in removing further articles. When it is desired to remove a further article, a fresh disposal bag 21 is placed over the short remaining severed part of the old disposal bag 21, and the new bag is fastened in place on the cylinder 24 by a rubber band. The remaining cap of the previous closure bag 28 can then easily ben pulled off from the interior of the enclosure member 13 to give access to the new disposal bag 21.

Figure 4A:
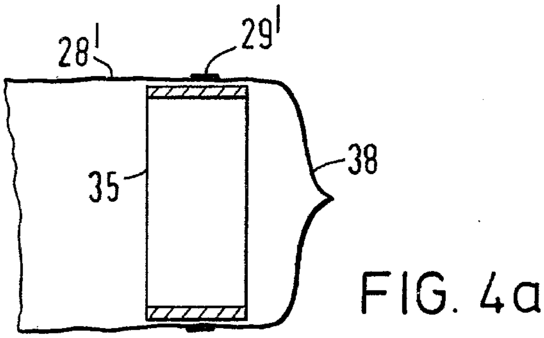
Figure 4B:
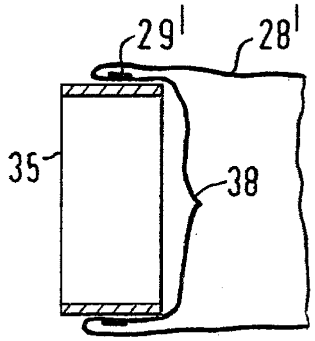
Figure 4C:
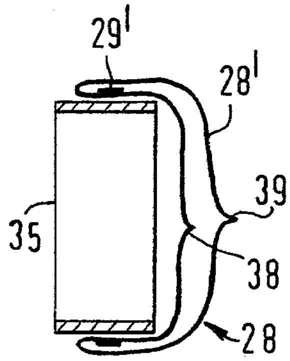

Referring now to FIGS. 4(*a*) to 4(*c*), there will be shown one convenient way of forming a closure bag for use in the method described with reference to FIGS. 3(*a*) to 3(*e*). Referring firstly to FIG. 4(*a*), a length of polyethylene tubing 28' is pulled over a rigid cylinder 35 and a flat seal is formed at one end indicated at 38. The backing member 29' is then formed by winding around the tubing 28' a length of adhesive backed neoprene or polyurethane foam tape.

As shown in FIG. 4(*b*), the next step is for the polyethylene tubing 28' to be folded back over itself so as to extend in the same direction as the sealed end 38 of the tubing. The final step as shown in FIG. 4(*c*) is that a further flat seal is produced along the tubing 28' at a position indicated at 39. The completed closure bag is then released by sliding the backing member 29' with the closure bag 28 off the rigid cylinder 35.

It is an advantage of the method according to the invention in both aspects, that contaminated articles are left in a sealed sterilised disposal bag by a method which does not require difficult, flat, continuous seals to be effected across a disposal bag, and does not rely upon cutting and taping of the ends of a severed disposal bag to effect secure seals.

The required closure bag containing the hoop member in the first aspect of the invention (described by way of example with reference to FIGS. 2(*a*) to 2(*d*)) can easily be provided by placing the hoop member in a length of flexible plastics tubing of wide diameter, and effecting seals across the tubing on either side of the hoop member. Although in these cases the seals are required to be flat seals, they can be made easily in laboratory conditions before the device is used in the hospital. Alternatively the closure bag may be made by a system corresponding generally to that described with reference to FIGS. 4(*a*) to 4(*c*).

Another advantage of the method and structure described in the embodiments of the invention shown, is that it allows a reduction in the length of the disposal bag 21 which is required compared with that normally needed with known methods of disposal. The space available in a hospital room is usually very limited so that the saving is of considerable value.

It is to be appreciated that all the Figures of the accompanying drawings are to be regarded as of a diagrammatic nature. For example the cylinder 24 shown in FIG. 1 omits the flared end, shown in the following Figures, which is provided to prevent slippage of the disposal bag.

I claim:

1. An isolator apparatus comprising:

an enclosure member for providing an environment isolated from the anbient environment;

said enclosure member having a transfer port for passage of objects out of the enclosure member;

a flexible disposal bag having one end coupled to the enclosure member around said transfer port;

a closure bag comprising a closed bag having a clean inner surface and containing a backing member in the form of a hoop, said closure bag being positioned within the disposal bag generally transverse to the disposal bag in a position such that the closure bag spans the hoop member to form a double walled barrier across the disposal bag and that part of the closure bag is sandwiched between the hoop member and the disposal bag; and means for effecting a sealing and cutting operation around the hoop member to cut through the disposal bag and the closure bag and to leave a portion of the closure bag sealed to the disposal bag on each side of the cut with the said clean surface of the closure bag exposed to the ambient environment, the article being sealed in the severed part of the disposal bag by one portion of the closure bag and the remainder of the disposal bag being closed by the other portion of the closure bag after the sealing and cutting operation.

2. Apparatus according to claim 1 in which the backing member comprises a hoop member which is a substantially rigid member adapted to be arranged with the said part of the closure bag sandwiched between the outside of the hoop member and the inside of the disposal bag, and adapted to allow the sealing and cutting step to be effected by application of a heating element around the hoop member with inward pressure on to the hoop member.

3. Apparatus according to claim 2 in which the hoop member comprises an inner, relatively stiff support portion, and an outer, relatively soft resilient layer allowing a good seal to be obtained by inward pressure of the heating element against the hoop member.

4. An isolator apparatus comprising:

an enclosure member for providing an environment isolated from the ambient environment;

said enclosure member having a transfer port for passage of objects out of the enclosure member;

a flexible disposal bag having one end coupled to the enclosure member around said transfer port;

a hollow former of approximately the same cross-section as the disposal bag;

a closure bag comprising a closed bag having a clean inner surface, the closure bag being mounted by a sliding fit on to one end of the hollow former in a position such that an adjacent pair of walls of the closure bag span one end of the former, and said hollow former extending from the enclosure member through the port into the disposal bag so that the closure bag forms a barrier across the disposal bag with a portion of the closure bag;

a pressure member positioned between the former and the closure bag for exerting, when activated, an outward pressure on the closure bag; and means for effecting a sealing and cutting operation around the disposal bag in the region of the closure bag by cooperation between the sealing and cutting means and the pressure member to cut through the disposal bag and the closure bag and to leave a portion of the closure bag sealed across the disposal bag on each side of the cut with the said clean surface of the closure bag exposed to the ambient environment.

5. An enclosure member according to claim 4 in which the closure bag contains a flexible backing member adapted to slide over the said former to position the closure bag to form the said barrier, and to cooperate with the cutting and sealing means.

6. A set of components for assembly into an isolator apparatus for providing an environment isolated from the ambient environment, the set of components comprising:

an enclosure member for providing an environment isolated from the ambient environment;

said enclosure member having a transfer port for passage of objects out of the enclosure member;

a flexible disposal bag having one end adapted to be coupled to the enclosure member around said transfer port;

a closure bag comprising a closed bag having a clean inner surface and containing a backing member in the form of a hoop adapted to be positioned within the disposal bag and to be arranged generally transverse to the disposal bag in a position such that the closure bag spans the hoop member to form a double walled barrier across the disposal bag and that part of the closure bag is sandwiched between the hoop member and the disposal bag; and means for effecting a sealing and cutting operation around the hoop member to cut through the disposal bag and the closure bag and to leave a portion of the closure bag sealed to the disposal bag on each side of the cut with the said clean surface of the closure bag exposed to the ambient environment, the article being sealed in the severed part of the disposal bag by one portion of the closure bag and the remainder of the disposal bag being closed by the other portion of the closure bag after the sealing and cutting operation.

7. A set of components for assembly into an isolator apparatus for providing an environment isolated from the ambient environment, the set of components comprising:

an enclosure member for providing an environment isolated from the ambient environment;

said enclosure member having a transfer port for passage of objects out of the enclosure member;

a flexible disposal bag having one end adapted to be coupled to the enclosure member around said transfer port;

a hollow former of approximately the same cross-section as the disposal bag;

a closure bag comprising a closed bag having a clean inner surface, the closure bag being adapted to slide on to one end of the hollow former so that an adjacent pair of walls of the closure bag span one end of the former, the former being of a size such as to allow advance of the former from the enclosure member through the port into the disposal bag so that the closure bag forms a barrier across the disposal bag with a portion of the closure bag sandwiched between the former and the inner surface of the disposal bag;

a pressure member positioned between the former and the closure bag for exerting, when activated, an outward pressure on the closure bag; and means for effecting a sealing and cutting operation around the disposal bag in the region of the closure bag by cooperation between the sealing and cutting means and the pressure member to cut through the disposal bag and the closure bag and to leave a portion of the closure bag sealed across the disposal bag on each side of the cut with the said clean surface of the closure bag exposed to the ambient environment.

8. A method of removing an article from an enclosure member providing an environment isolated from the ambient environment comprising the steps of passing the article through a port in the enclosure member into a disposal bag communicating with the port and sealed around the port, positioning within the disposal bag a closure member comprising a closed bag having a clean inner surface, arranging the closure bag across the disposal bag to form a double-walled barrier between the port of the enclosure member and the article in the disposal bag, and effecting a sealing and cutting operation around the disposal bag in the region of the closure bag to cut through the disposal bag and the closure bag and to leave a portion of the closure bag sealed across the disposal bag on each side of the cut with the said clean surface for the closure bag exposed to the ambient environment, the article being sealed in the severed part of the disposal bag by one portion of the closure bag and the remainder of the disposal bag being closed by the other portion of the closure bag.

9. A method according to claim 8 including the steps of providing within the closure bag a backing member for cooperation with a sealing and cutting device for effecting the sealing and cutting step, and arranging part of the closure bag and part of the disposal bag in a sandwich between the backing member and the sealing and cutting device during the sealing and cutting operation.

10. A method according to claim 9 including the steps of providing a hoop member as the said backing member and arranging the hoop member generally transverse to the disposal bag in a position such that the closure bag spans the hoop member and part of the closure bag is sandwiched between the hoop member and the disposal bag.

11. A method according to claim 10 including the steps of providing a substantially rigid member as the said hoop member, and applying inward pressure against the sandwiched portions of the closure bag and the disposal bag against the rigid hoop member during the sealing and cutting operation.

12. A method according to claim 11 in which the sealing and cutting operation is effected by applying a heated cutting element to the outer surface of the disposal bag around the hoop member so that there is provided a sandwich of elements comprising, in the order given, the heating element, a part of the disposal bag, a part of the closure bag, and the hoop member.

13. A method according to claim 9 including the steps of providing a flexible member as the said backing member, sliding the backing member onto one end of a hollow former of approximately the same cross-section as the disposal bag so that an adjacent pair of walls of the closure bag span one end of the former, advancing the former from the enclosure member through the port into the disposal bag so that the closure bag forms a barrier across the disposal bag with a portion of the closure bag sandwiched between the backing member and the inner surface of the disposal bag applying around the disposal bag in the region of the backing member a cutting and sealing device, activating a pressure member positioned between the former and the closure bag so as to exert an outward pressure on the backing member to bring the adjacent layers of the closure bag and the disposal bag into operative contact with the cutting and sealing device, and effecting the said sealing and cutting operation.

14. A method according to claim 13 in which the step of activating the pressure member comprises inflating an expandable pressure member which is arranged around the former.

15. An isolator component suitable for use in accordance with the method as set out in claim 1 the component consisting of a closure bag comprising a flexible closed bag having a clean inner surface and containing a backing member, the bag being adapted for a sealing and cutting operation around the backing member within a flexible disposal bag extending from a port in an enclosure member for providing an environment isolated from the ambient environment.

16. An isolator component as claimed in claim 15 in which the backing member comprises a hoop member which is a substantially rigid member adapted to be arranged with part of the closure bag sandwiched between the outside of the hoop member and the inside of the disposal bag in use, and adapted to allow the sealing and cutting step to be effected by application of a heating element around the hoop member with inward pressure on to the hoop member.

17. An isolator component as claimed in claim 15 in which the closure bag contains a flexible backing member adapted to slide over a hollow former of approximately the same cross-section as the said disposal bag with which the closure bag is adapted to be used, the flexible backing member being adapted to cooperate with cutting and sealing means for use in the said sealing and cutting operation.

* * * * *